United States Patent
Kassebaum et al.

(10) Patent No.: US 8,722,396 B2
(45) Date of Patent: May 13, 2014

(54) BIOREACTOR ASSEMBLY FOR CULTURE OF PHOTOAUTOTROPHIC ALGAE

(75) Inventors: William R. Kassebaum, Indianapolis, IN (US); John A. Kassebaum, Indianapolis, IN (US)

(73) Assignee: Algaeon, Inc, Indianapolis, IN (US)

( * ) Notice: Subject to any disclaimer, the term of this patent is extended or adjusted under 35 U.S.C. 154(b) by 597 days.

(21) Appl. No.: 12/916,572

(22) Filed: Oct. 31, 2010

(65) Prior Publication Data

US 2011/0104790 A1 May 5, 2011

Related U.S. Application Data

(60) Provisional application No. 61/257,432, filed on Nov. 2, 2009.

(51) Int. Cl.
*C12M 1/00* (2006.01)
*C12M 1/04* (2006.01)
*C12N 1/12* (2006.01)

(52) U.S. Cl.
USPC .................. 435/293.1; 435/289.1; 435/292.1; 435/257.1

(58) Field of Classification Search
None
See application file for complete search history.

(56) References Cited

U.S. PATENT DOCUMENTS

| 4,868,123 | A  | * | 9/1989  | Berson et al. ............... 435/286.6 |
| 6,416,993 | B1 | * | 7/2002  | Wexler et al. .............. 435/262.5 |
| 6,602,703 | B2 | * | 8/2003  | Dutil .......................... 435/292.1 |
| 2003/0059932 | A1 |   | 3/2003  | Craigie et al. |
| 2003/0228684 | A1 |   | 12/2003 | Burbidge et al. |
| 2008/0286851 | A1 |   | 11/2008 | Whitton et al. |

* cited by examiner

*Primary Examiner* — David M Naff
(74) *Attorney, Agent, or Firm* — Tony A. Gibbens; Brannon Sowers & Cracraft PC

(57) ABSTRACT

A photobioreactor assembly, including a first generally horizontal manifold, a second generally horizontal manifold positioned below the first generally horizontal manifold, an array of generally parallel, generally transparent tubes extending between the manifolds, an air supply operationally connected to at least one manifold, a water filter, a water purifier, a water supply operationally connected to the water purifier, a pH sensor positioned to measure the pH in the array, and an electronic controller operationally connected to the pH sensor, the air supply, the water purifier, and the water supply. Each respective tube is connected in fluidic communication with the first horizontal manifold, and each respective tube is connected in fluidic communication with the second horizontal manifold.

12 Claims, 12 Drawing Sheets

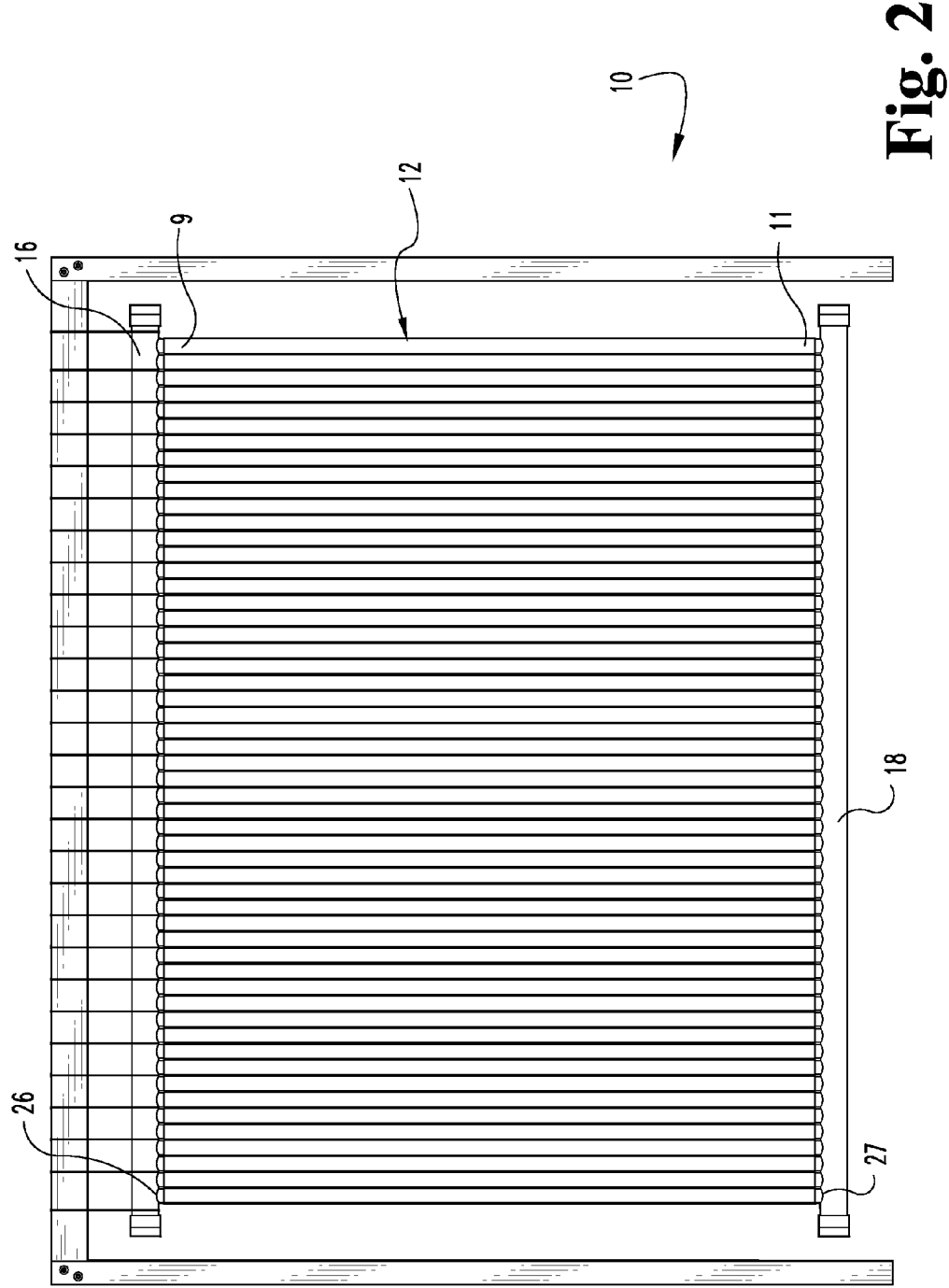

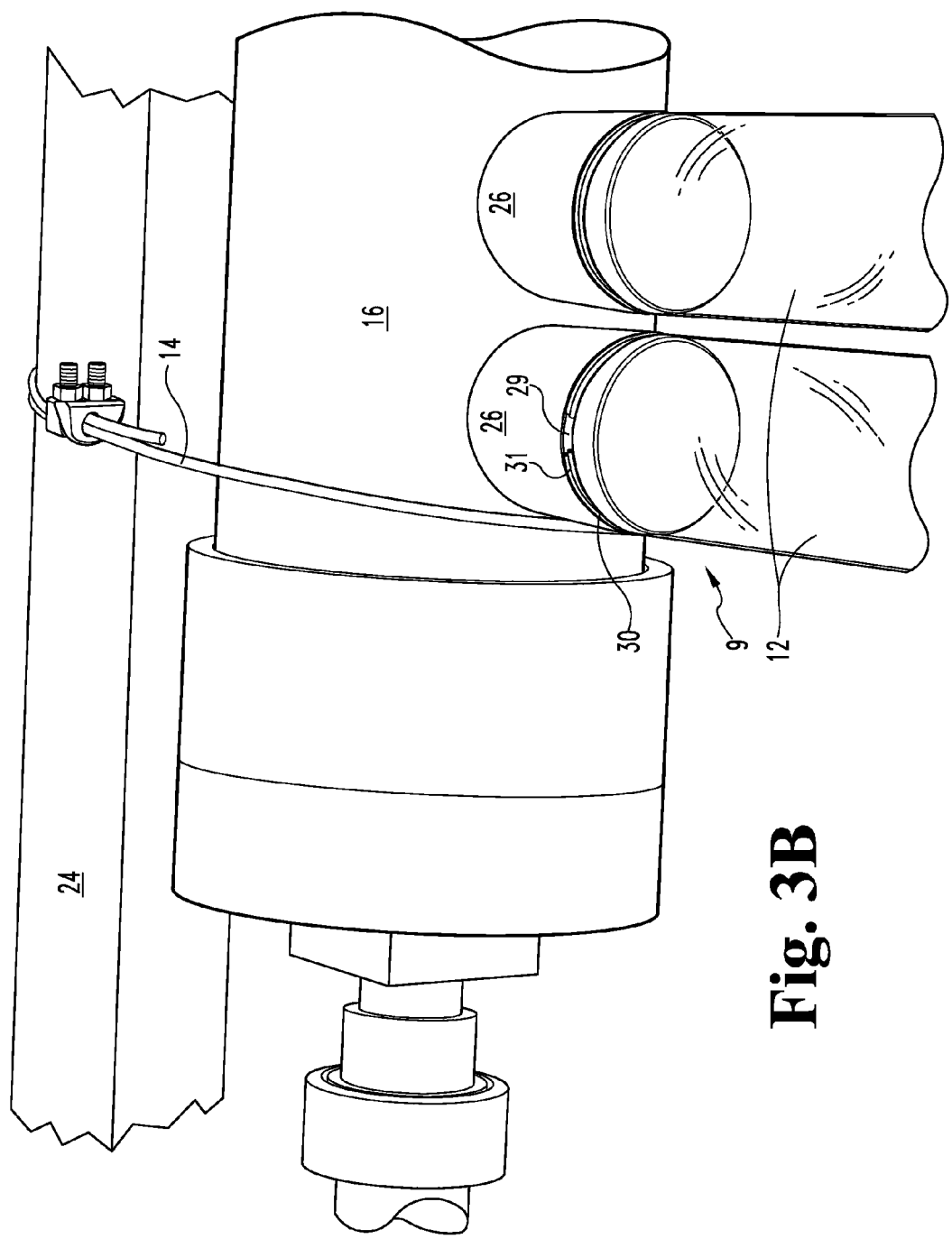

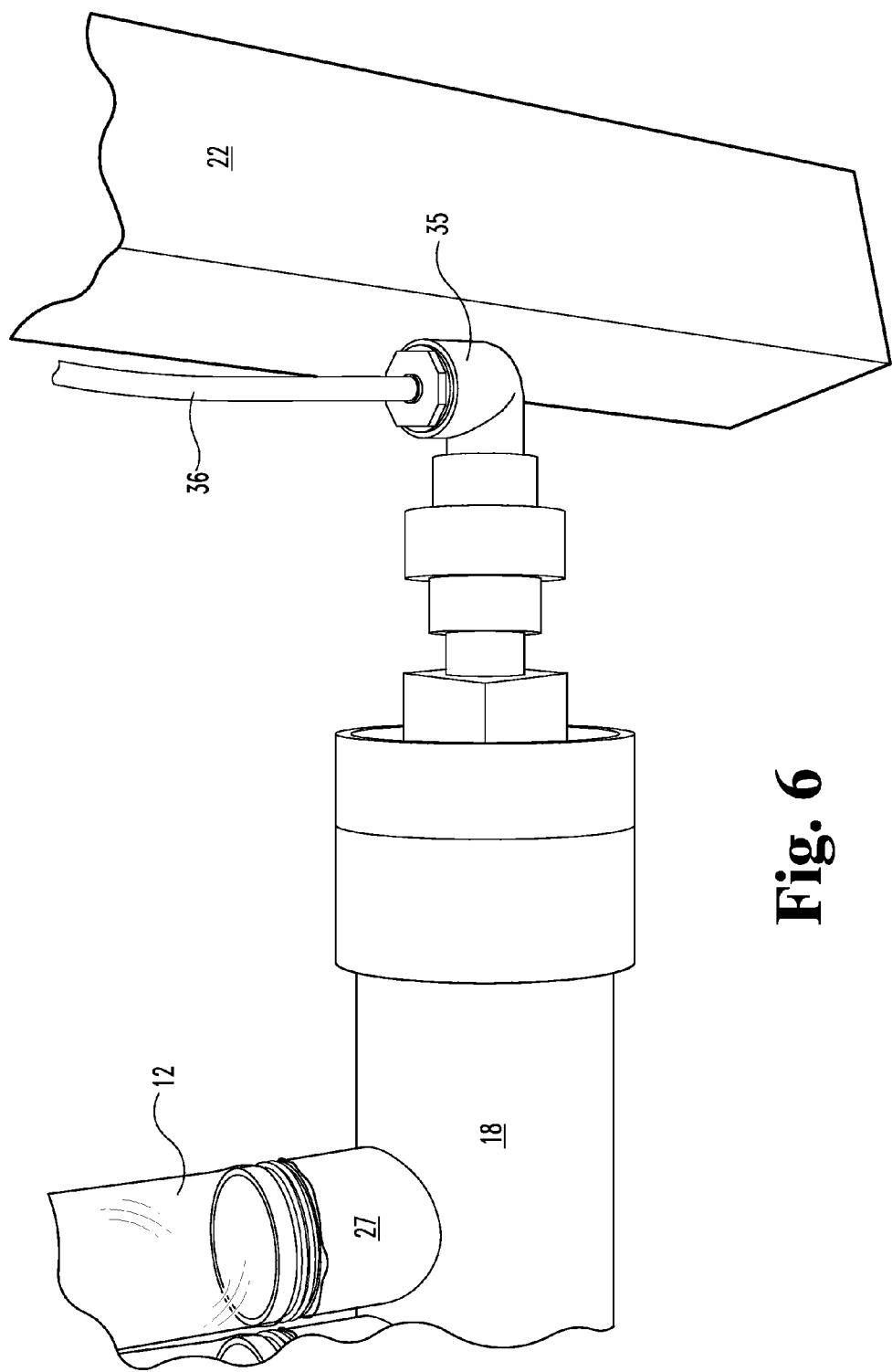

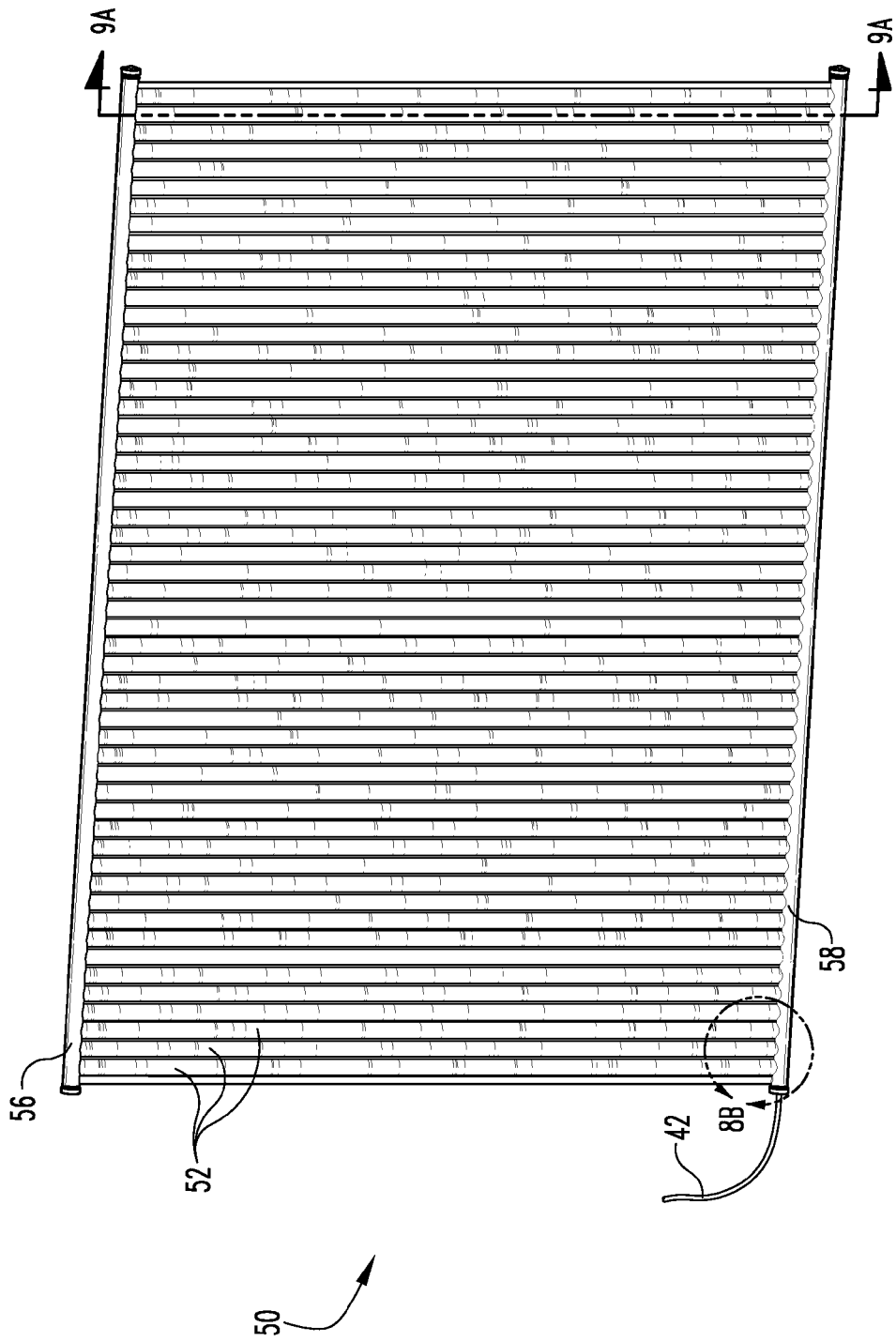

BIOREACTOR ASSEMBLY FOR CULTURE OF PHOTOAUTOTROPHIC ALGAE

CROSS-REFERENCE TO RELATED APPLICATIONS

This application claims priority to co-pending U.S. Provisional Patent Application Ser. No. 61/257,432, filed on Nov. 2, 2009.

TECHNICAL FIELD

The present novel technology relates generally to the field of energy, and, more particularly, to bioreactors for efficiently growing, cultivating and harvesting algae and their useful fuel oils in a phototrophic algae production process.

BACKGROUND

Due to dwindling supplies coupled with increasing demand, the price of oil has, and will continue to increase substantially over the years. The increasing price of oil, along with an increased scrutiny on the effects of greenhouse gas emissions, has led to the evaluation of alternative fuel sources to meet the energy demands and address environmental concerns. One such alternative fuel is the production of crude oil and biodiesel from vegetative precursors, such as algae.

A principal component of algae's composition is lipid oil which can be converted into a crude-type oil, consisting primarily of single-chain hydrocarbons or triglyceride and diglyceride fats and oils, for biodiesel feedstock. Algae has the benefit of being able to be grown in massive quantities with very little environmental impact. All that is needed to grow algae is water, appropriate nutrients, sunlight and carbon dioxide. Thus, as compared to petroleum, oil and biodiesel produced from algae are not a limited resource, because algae can be continuously grown in mass quantities for fuel production. Moreover, as compared to food crop biodiesel and ethanol produced from feed crops (i.e., grains), the production of algae does not drive up the price of certain food products and has a higher level of efficiency. For example, soy or corn yields approximately 70-100 and 150-300 gallons of fuel per acre per year, respectively. In contrast, certain algae species can yield in excess of 10,000 gallons of fuel per acre per year.

In addition, algae can provide several other benefits. For example, algae can yield specialty chemicals and/or pharmaceuticals (i.e., plastic resins (such as PHA and PHB), ketones, acetone, beta-carotene and Omega-3 and the like), nutrients, and a food source for animals, fish and humans. The challenge for producers of algae is not only to identify the most efficient strains of algae to use for the desired end-product, but also to determine how algae best can be grown to meet the demand for such end-products.

The most natural system for growing algae is the open-pond system (e.g., raceway ponds or natural ponds). Open-pond systems allow for algae growth in its natural environment and minimize environmental impact. While an open-pond system offers a low-cost algae production environment with very little environmental impact, open-pond systems inherently present too many variables to be controlled for maximized algae production. For example, open-pond systems are more susceptible to contamination from bacteria or other organisms that can stunt algae growth and make it difficult to target desired species of algae. Further, algae need to be shielded from bad weather and the water needs to be adequately stirred to promote algae growth, which is difficult and expensive to control in open-pond systems. As a result of all of these variables, open-pond systems suffer from low and/or inconsistent productivity levels.

In attempts to maximize yield and increase the speed of algae production, algae producers have utilized photoautotrophic and heterotrophic methods of algae production. Photoautotrophic methods utilize light to produce biomass, while heterotrophic methods involve algae consumption of sugars to produce biomass. Photoautotrophic algae producers use closed-loop systems, such as bioreactors or closed tank systems. Bioreactors involve the use of an array of vessels, typically bags or tubes, filled with an algae culture and media to maximize sun exposure and algae production. Closed tank systems involve the use of round drums and a controlled environment to maximize algae production. Heterotrophic systems, such as fermentation systems, are also being tested and developed in attempts to maximize the production of algae. The problems with all of these systems to date is that they each suffer from extremely high production costs that are so cost prohibitive that only small scale uses of these systems are economically feasible.

For photoautotrophic algae production methods, the focus is on optimizing photosynthesis to promote algae growth. Plants derive energy from sunlight and use that energy to convert carbon dioxide and water into biomass. Uncultivated macroscopic green plants have an energy utilization efficiency of approximately 0.2% (i.e., 0.2% of incident sunlight is utilized by the plant to convert water and carbon dioxide into biomass). Plants species can be classified by referring to their carbon fixation process (e.g., $C_3$-cycle plant species and $C_4$-cycle plant species), which is the first step of converting sunlight to biomass in photosynthetic organisms. Plant cultivation can improve energy utilization to a range of 1-2% for $C_3$-cycle plant species and up to about 8% for the most productive $C_4$-cycle plant species (e.g., sugarcane). Uncultivated microscopic green algae (typically C3-cycle plants) are more efficient than macroscopic plant species and can average as much as 6.2% energy utilization efficiency. Thus, by cultivating algae in controlled environments, the energy utilization efficiency can be increased even more and the rates for growing algae can substantially be increased.

Algae grows best at low light levels because at low light levels, algae photoefficiency can be as high as 60% to 80%. Counter-intuitively, high light levels decrease production, because algae respond to high light levels by protecting themselves from excessive radiation through the mechanisms of photoinhibition and photorespiration. Photoinhibition is the production of light absorbing materials to protect the algae's light harvesting chlorophyll antennas from damage caused by light over-saturation. Photorespiration essentially short-circuits the photosynthesis process because of excess production of oxygen. The result is that oxygen out-competes carbon dioxide at the site of the Rubisco enzyme and glucose cannot be produced. Thus, to keep algae biomass production occurring at a high rate, the light levels must be low enough so that carbon fixation does not exceed the concentration dependent diffusion rates of carbon dioxide into the algae's chloroplasts.

It also needs to be kept in mind that photosynthesis does not use a large proportion of the sun's broad light production. Even though the sun has its highest output in the green portion of the spectrum (around 550 nm), algae only use the light in portions of the red and blue regions of the spectrum. The inactive portions of the spectrum, such as ultraviolet and infrared portions, contain quite a bit of energy which constitutes a large fraction of the solar output. Unfortunately, these inactive portions often cause more harm than good in the algae growing process because ultraviolet radiation can cause damage and resulting oxidative stress. Infrared radiation can also cause significant and potentially damaging over-heating of the algae.

To prevent the problems associated with over radiation, algae producers can use some means of shifting the sun's illumination to match the photosynthetic action spectra. Such tools can involve the use of light sources, such as highly efficient blue and red LEDs, that effectively and efficiently produce photosynthetically active radiation (PAR). However, the use of such light sources have the negative impact of increasing the cost of production because they increase the amount of energy needed to power the production process.

Thus, a photobioreactor system and method for producing algae is still needed that optimizes the available sunlight and maximizes the production of algae in a low-cost, efficient manner in order to make large scale algae production economically feasible. The present novel technology addresses this need.

BRIEF DESCRIPTION OF THE DRAWINGS

The features and advantages of this disclosure, and the manner of attaining them, will be more apparent and better understood by reference to the following descriptions of the disclosed system and method, taken in conjunction with the accompanying drawings, wherein:

FIG. 2 is a front elevation view of an array of elongated reaction tubes used in the photobioreactor system of FIG. 1.

FIG. 3B is an enlarged partial perspective view of the upper manifold of the photobioreactor system of FIG. 1.

FIG. 6 is a partial perspective view of the lower manifold and air inlet of the embodiment of FIG. 1.

FIG. 8A is a perspective view of a second embodiment photobioreactor system of the present invention.

DETAILED DESCRIPTION

For the purposes of promoting an understanding of the principles of the present disclosure, reference will now be made to the embodiments illustrated in the figures, and specific language will be used to describe the same. It will nevertheless be understood that no limitation of the scope of this disclosure is thereby intended.

Figure 1:
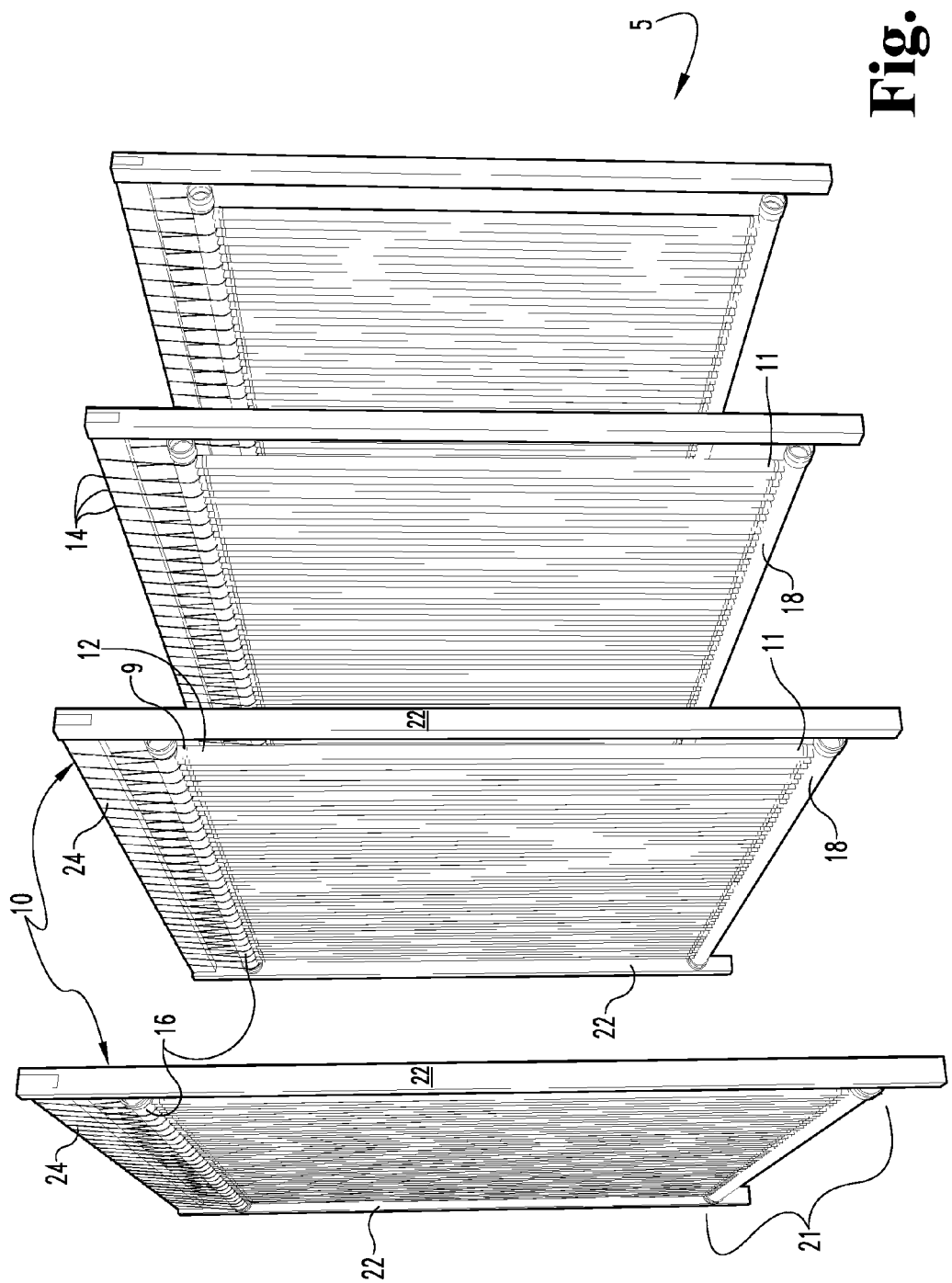
FIG. 1 is a perspective view of a first embodiment photobioreactor system according to the present disclosure.

FIGS. 1-7 and 10 illustrate a first embodiment photobioreactor system 5 for the mass production of algae in an efficient and cost effective manner. As shown in FIG. 1, photobioreactor system 5 includes one or more arrays 10 of vertically arranged vessels or tubes 12, each respective tube 12 attached at its top end 9 to top manifold 16 and at its lower end 11 to bottom manifold 18. Each manifold typically comprises a generally rigid pipe with a plurality of generally cylindrical openings 26, 27 (shown in FIG. 2). The openings 26, 27 are typically evenly spaced and may be raised to engage the tube ends 9, 11. In this embodiment, such pipes are polyvinyl chloride (PVC) pipes, but it should be understood that any type of pipe material may be selected.

Still referring to FIG. 1, photobioreactor system 5 is attached to a frame 21 that comprises two vertical beams 22 and a top rail 24. In this embodiment, top rail 24 and vertical beams 22 are made of wood. While vertical beams 22 and top rail 24 are made of wood in this embodiment, it will be appreciated that any other structural material that is of sufficient strength to hold photobioreactor system 5 can be used to construct the frame. Typically, vertical beams 22 are anchored into the ground by cement, but it will be appreciated that vertical beams 22 could be mounted to a base or anchored to the ground in any number of ways known to those skilled in the art. Top rail 24 is attached to vertical beams 22 by any suitable attachment means, including, but not limited to, nails, bolts, or screws. Each end of the top rail 24 is attached at the top end of both vertical beams 22 to form the rectangular frame depicted in FIG. 1. Top manifold 16 may be attached to top rail 24 utilizing any number of attachment means known in the art. As shown in FIGS. 1-3, top manifold 16 is connected to top rail 24 by a plurality of wire riggings 14 that are wrapped around both top manifold 16 and top rail 24.

Referring to FIGS. 1 and 2, tubes 12 each define an individual cellular bioreactor and are typically each arranged vertically along the photobioreactor system's 5 vertical, Y-axis. Tubes 12 have a similar structure as a pipe in that each tube 12 is a hollow, generally cylindrical body. Prior art tubular bioreactors had the drawback of being constructed from solid or inflexible pipe materials, such as glass, acrylic, polycarbonate, transparent PVC, and other similar materials. The cost of such materials is expensive and has prevented tubular bioreactors from being used on larger scales. Tubes 12 of the photobioreactor system 5 are each produced from thin, inexpensive films. The tubes 12 are typically transparent (e.g., at least 90% transmissive) to allow for sunlight to enter into the tube 12. Tubes 12 are typically opaque to UV radiation, so that the tubes 12 will not degrade quickly and will not expose algae to unwanted UV. Tubes 12 typically have tensile strength at the operational temperatures of the photobioreactor system 5 sufficient to oppose the pressure of the tube 12 being filled with fluid and typically have sufficient toughness to resist tearing or rupturing when punctured, so that the tube 12 can be easily patched if a leak occurs.

Low density polyethylene (LDPE) plastic films are well suited to form each tube 12. Tubes 12 constructed from such plastic films have a useful stretching property. As such films elongate along the axial direction, the film will contract tangentially and radially. As a result, when tubes 12 are filled with liquid, the tubes 12 do not form a tear-drop shape or 'pillow-out' at the bottom, but instead, typically remain cylindrical along their entire length. LDPE films are also effective because they can be made to be resistant to UV rays and normally have a life-cycle in excess of four years when used outdoors.

In addition to LDPE films, it will be appreciated by those skilled in the art that other films with similar characteristics to LDPE films can be used to create tubes 12. Examples of other film materials that can be used include ethylene tetrafluoride (ETFE, a form of Teflon), polyethylene terephalate (PET), and vinyl films. ETFE films are another useful film because they are optically clear, durable, and highly radiation resistant with a life-cycle of 20 to 50 years when used outside. PET films have been found to be susceptible to tearing and if used, are typically reinforced or layered with another plastic to avoid tearing.

By selecting films with sufficient tensile strength at the photobioreactor system's 10 operating temperatures, the amount of plastic resin required may be substantially reduced to yield substantial cost savings. For example, LDPE and ETFE films can be used at thicknesses as low as 2 mils to create tubes 12, which still have sufficient tensile strength to hold a 15 foot high column of fluid with little difficulty. While LDPE and ETFE films can be used as low as 2 mils in thickness, the LDPE and ETFE films typically have a thickness of a least 6 mils such that resultant tubes 12 are more durable and easier to handle without resulting in damage during the algae production process.

The dimensions of each of the tubes 12 are only limited by the practical limitations of the photobioreactor system 5. For example, with taller and wider tubes 12, more air is needed to stir the liquid, the tubes 12 take up more space, and it is more difficult and time consuming to perform maintenance on the system 5. Shorter tubes 12 support higher algae densities during growth but require a greater air volume to aerate the culture and are less effective at dissolving carbon dioxide and removing air due to the shorter water path. While tubes 12 can be of any desired length that can be managed during the algae production process, tubes 12 in this particular embodiment are about ten feet in length and can range between about five to fifteen feet in length. Similarly, while tubes 12 have a diameter of any size that can easily be managed during the algae production process, tubes 12 in this particular embodiment typically have diameters ranging from about one to about twelve inches.

As shown in FIGS. 1-2, each tube 12 has a top end 9 connected in fluidic communication with top manifold 16 and a bottom end 11 connected in fluidic communication with bottom manifold 18. Both top and bottom manifolds 16, 18 have a plurality of cylindrical typically raised openings 26 and 27 that extend (typically vertically) from the horizontal axis of each of the top and bottom manifolds 16, 18. In this manner, each respective opening 26 and 27 is positioned substantially perpendicular to the horizontal axis of both the top and bottom manifolds 16, 18. Both the top and bottom manifolds 16, 18 have an equal number of openings 26, 27. Openings 27 of the bottom manifold 18 are positioned so that each opening 27 faces and is aligned along the same vertical plane with a corresponding opening 26 positioned on top manifold 16. Referring to both FIGS. 1 and 2, this orientation allows for each tube 12 to be positioned vertically along the Y-axis of the photobioreactor system 5, when each respective tube's 12 top end 9 is connected to one of the openings 26 of the top manifold 16 and the tube's 12 bottom end 11 is connected to a respective corresponding opening 27 of the bottom manifold 18.

Figure 3A:
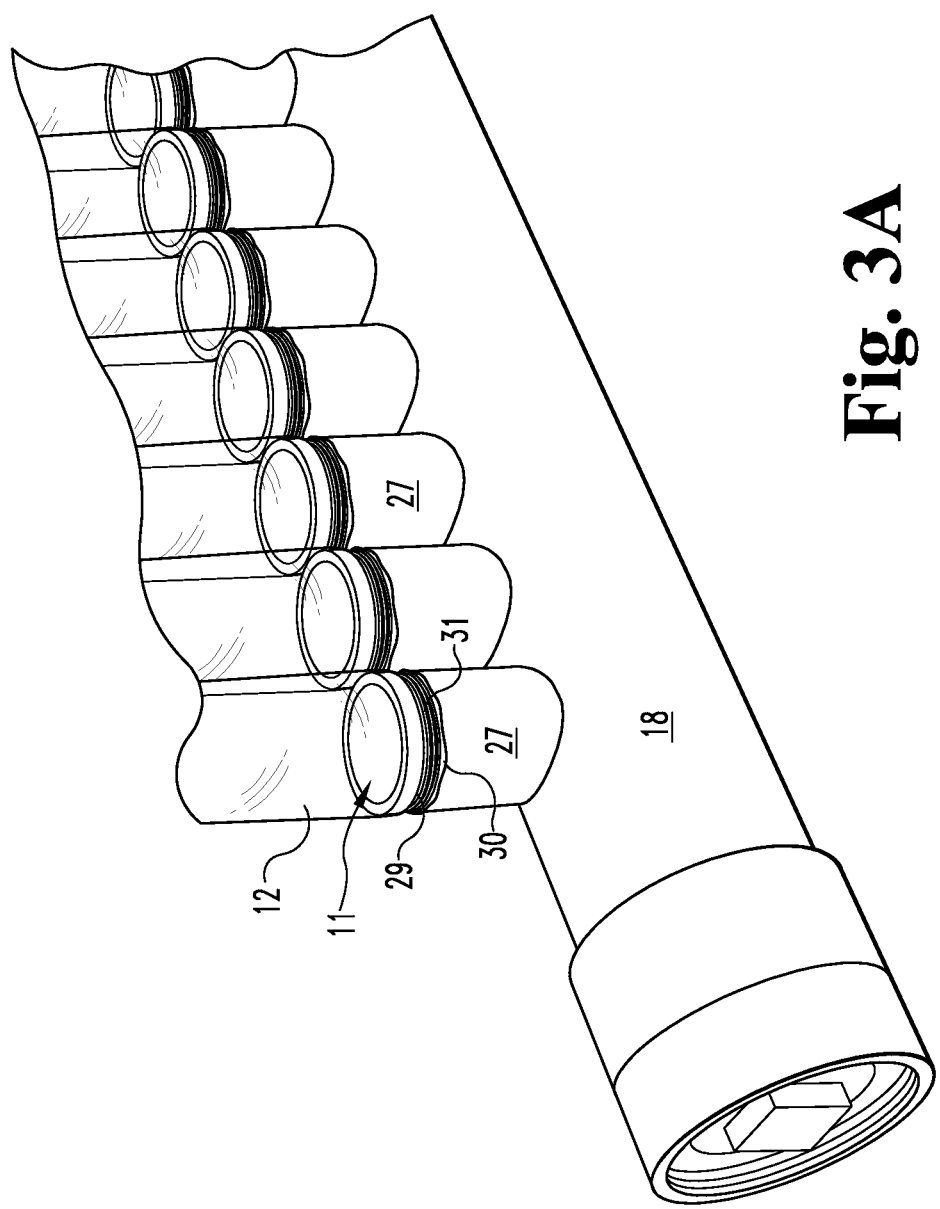
FIG. 3A is an enlarged partial perspective view of the lower manifold of FIG. 1.

FIG. 3A shows a close up view of the tubes 12 connected to opening 27 of bottom manifold 18. The diameter of tube 12 is typically greater than the diameter of opening 27, so that the bottom end 11 of each tube 12 can slip over and engage a respective raised, cylindrical opening 27. In this manner, opening 27 fits and resides within the bottom end 11 of tube 12. Each opening 27 typically has a groove 29 positioned below the lip of opening 27 and around the outer circumference of the opening 27. A compressible material 30, such as a rubber band or gasket, is placed in the groove 29. After the bottom end 11 is slipped over opening 27, wire rigging 31 is then tightened around the external circumference of both the bottom end 11 of tube 12 and the raised, cylindrical opening 27 at the position of the groove. As the wire rigging 31 is tightened, the gasket material compresses to define a non-leaking seal between the tube 12 and opening 27. In this manner, the tube 12 is held in place around the opening 27 and is connected to bottom manifold 18 to form a pathway that allows fluid and gas to pass in between the tubes 12, openings 27 and bottom manifold 18.

Likewise, as shown in FIG. 3B the top ends 9 of each tube 12 are attached to the raised, cylindrical openings 26 that each correspond in location to the cylindrical opening 27 that the bottom end 11 of each of the tubes 12 is attached to on the bottom manifold 18. Each top end 9 is connected to its respective cylindrical opening 26 in the same manner as each bottom end 11 is connected to cylindrical opening 27 as described above. The diameter of tube 12 is bigger than the diameter of opening 26 so that the top end 9 of tube 12 can slip over the raised, cylindrical opening 26, so that opening 26 fits into and resides within tube 12. Each opening 26 has a groove 29 positioned below the lip of opening 26 and around the outer circumference of the opening 26. A compressible material, such as a rubber band or gasket, is placed in the groove 29. After the top end 9 is slipped over opening 26, wire rigging 31 is then tightened around the external circumference of both the top end 9 of tube 12 and the raised, cylindrical opening 26 at the position of the groove 29. As the wire rigging is tightened, the gasket material compresses to define a non-leaking seal between tube 12 and opening 26. In this manner, the tube 12 is held in place around the opening 26 and is connected to top manifold 16 to form a pathway that allows fluid and gas to pass in between the tubes 12, openings 26 and top manifold 16. Once system 5 is assembled, it is filled with (typically filtered and/or sterilized) water, the desired algae culture(s) is added, a measured amount of nutrients are added, fertilizer is added if desired, and (typically filtered and/or sterilized) air (with our without additional $CO_2$) is bubbled therethrough. The pH of the water may be controlled by the level of $CO_2$ in the air stream, chemically, or by any convenient means.

Figure 4:
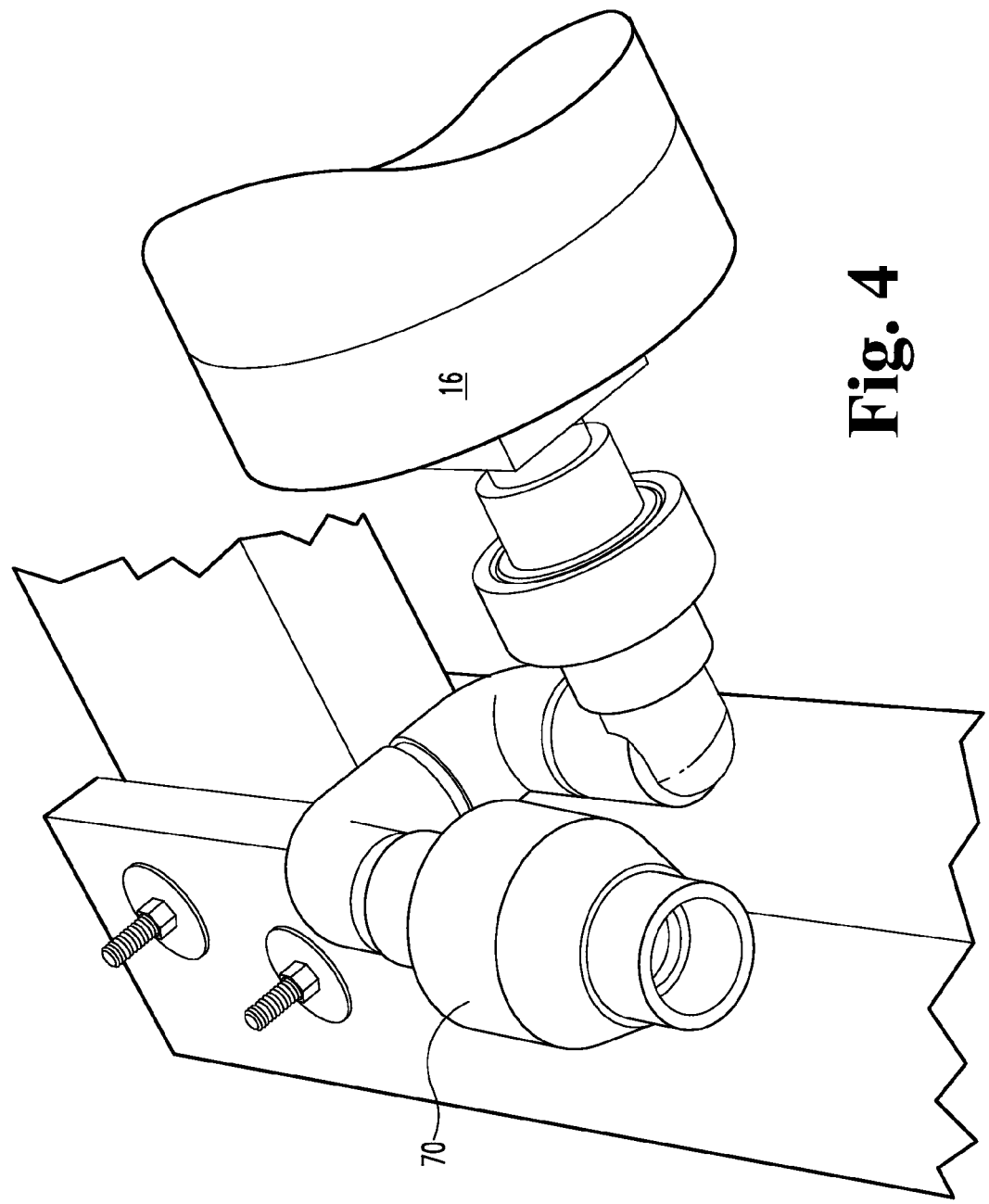
FIG. 4 is an enlarged partial perspective view of a relief valve from the photobioreactor systems of FIG. 1.

Photobioreactor system 5 is a typically closed, aseptic system operating under positive pressure. As shown in FIG. 4, one or more air exhaust valves 70 are connected in pneumatic communication with upper manifold 16 to allow for excess oxygen to escape the photobioreactor system 5. While it will be appreciated by one skilled in that art that any type of exhaust valve can be used, an exhaust valve 70 that can build up an adequate amount of positive pressure in the system 5 is typically selected. For example, in this embodiment, valve 70 does not open until the gas build up in the system 5 reaches about one-half pound of pressure. In this manner, valve 70 is used to build up positive pressure in the photobioreactor system 5 to prevent contaminants from entering into the system 5. In addition to operating the photobioreactor system 5 under positive pressure, photobioreactor system 5 typically utilizes a plurality of filters and inlet and outlet valves to establish and maintain the aseptic environment.

Figure 5A:
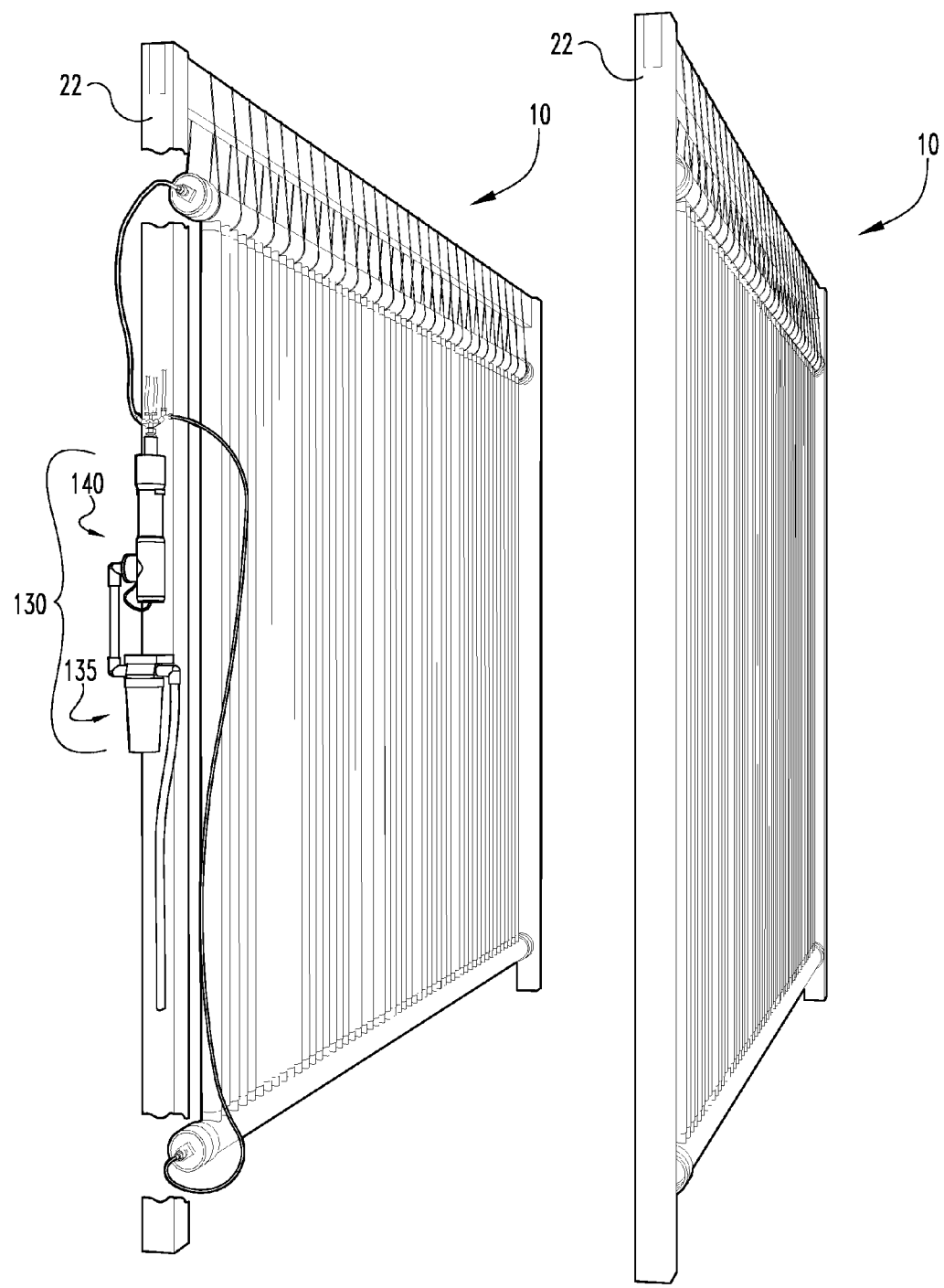
FIG. 5A is a perspective view of the arrays of a photobioreactor system according to the embodiment of FIG. 1.
Figure 5B:
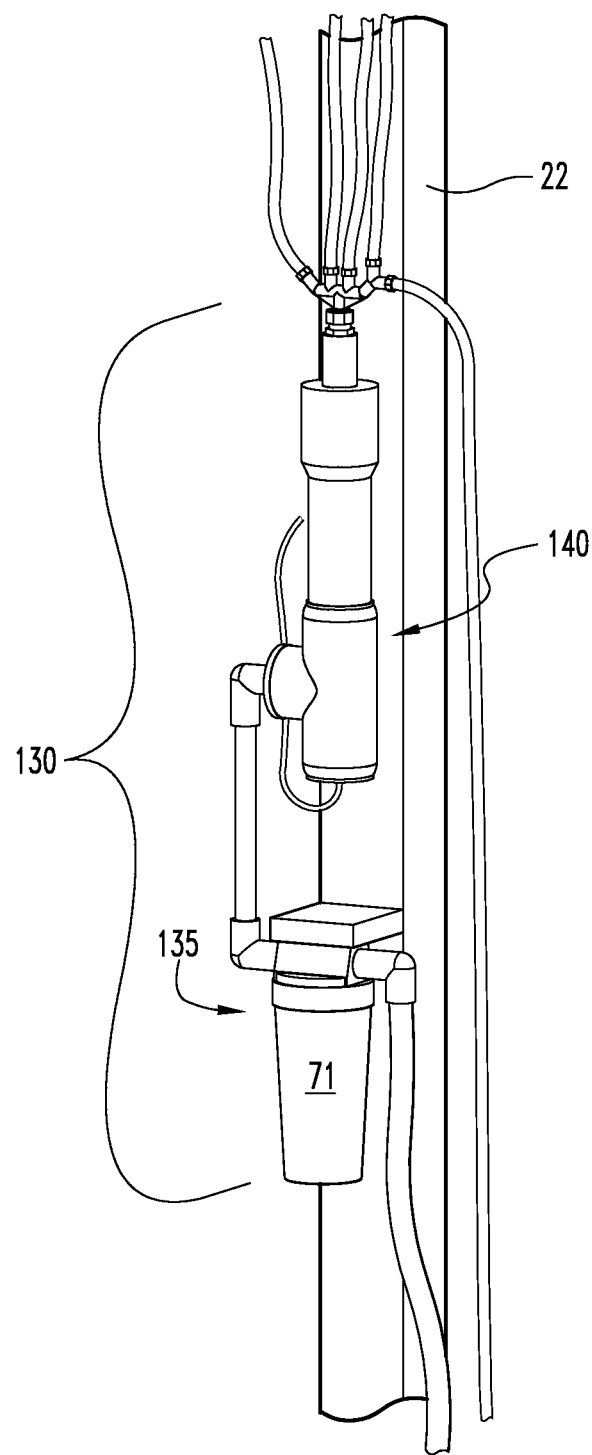
FIG. 5B is an enlarged partial view of FIG. 5A showing a purifier system.

FIGS. 5A and 5B illustrate two photobioreactor arrays 10 in wherein arrays 10 are filled with an algae culture and with liquid media made up of sterile water and fertilizer respectively. The media water can be provided by any water source 120 or can be recycled from previous cultures. Prior to being added to photobioreactor array 10, the water is passed through a filter and UV sterilization bank to remove particles and neutralize contaminants. As shown in FIG. 5B, water filtration system 130 comprises a micro-filter 135 and a UV sterilization bank 140. Filtration system 130 is used to filter water to remove biological contaminating particles (e.g., bacteria, mold, fungus, and other micro-algae species) and the water is irradiated with UV-B or UV-C light in the UV sterilization bank 140 to ensure the media water is sterile. It will be appreciated that any suitable water treatment filters 135 can be used and that the UV sterilization bank 140 can be set to known irradiation levels to eliminate the biological contaminants of concern.

The fertilizer used in the photobioreactor system 5 will largely depend on the nutrient requirements of the particular species of algae being cultivated. The fertilizer is typically added to the filtered media water and then fed into the photobioreactor system 5 at the same time as the media water. The media water and fertilizer are typically added through a water tube and an inlet valve. If the media water is recycled from a previous culture, the media water may have some fertilizer still present. In such cases, the fertilizer concentrations in the media water are measured and additional fertilizer is added, only as needed, to add the desired nutrients to the media prior to re-introduction into a photobioreactor array 10.

Aeration of the photobioreactor system 5 is performed to facilitate gas exchange for removal of excess oxygen and deliver carbon dioxide to promote the growth of the algae. Air, with or without additional carbon dioxide, is added to the photobioreactor system 5 to control the pH of the culture and to promote algae growth. FIG. 6 shows a close up view of the gas inlet port 35. Prior to entering into the bottom manifold 18, air (with or without additional carbon dioxide) flowing through a gas inlet tube 36 passes through a microbe filter 34 (See FIG. 10) to remove any potential contaminants prior to being introduced into the photobioreactor system 5. Gas inlet tube 36 feeds air (with or without additional carbon dioxide) to the lower manifold through gas inlet valve 35 to aerate the culture. To avoid contamination, the gases introduced into the photobioreactor system 5 are typically sterilized and/or or passed through a filter, such as a HEPA filter of 0.2 micron size or less.

Figure 7:
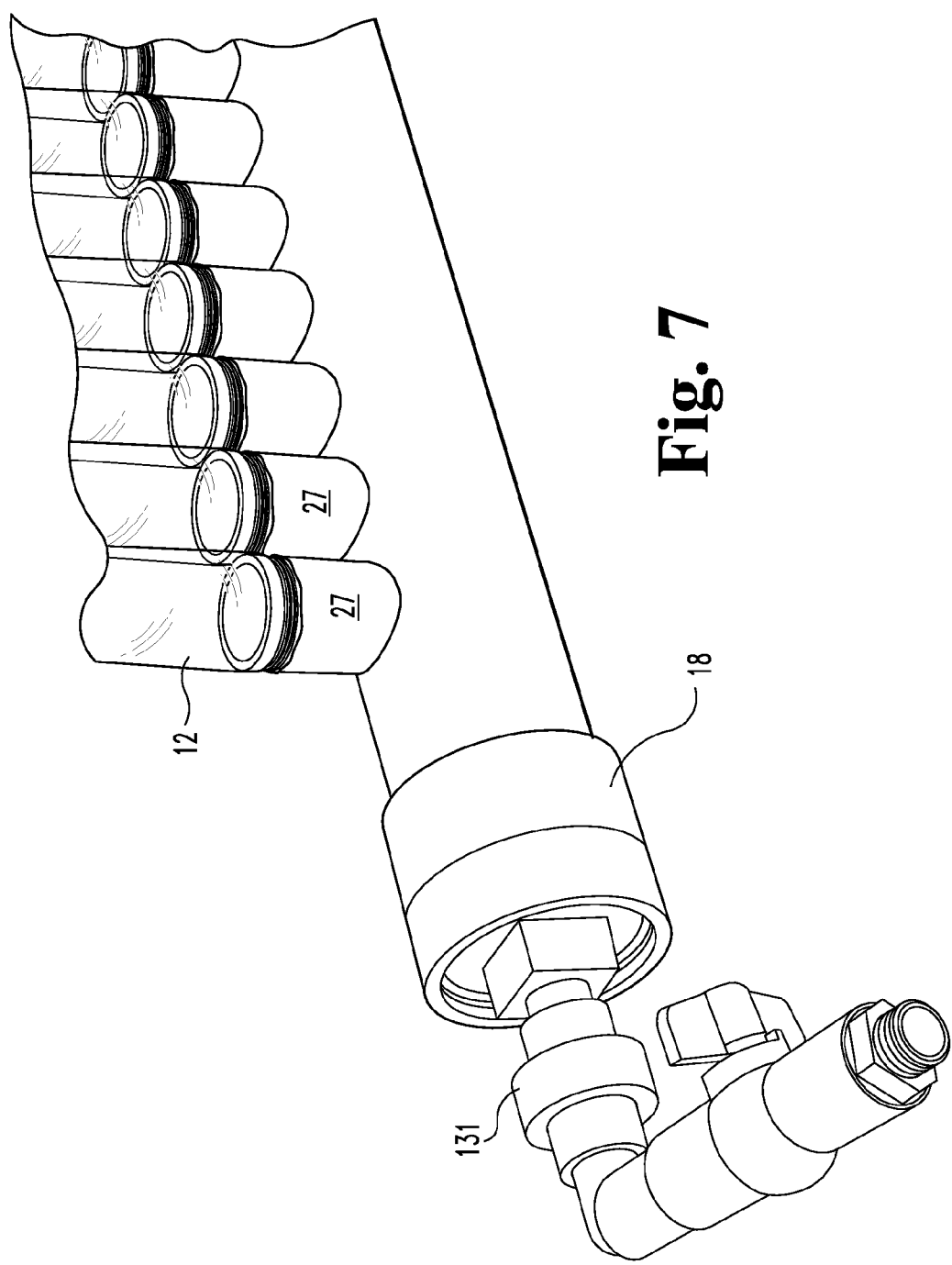
FIG. 7 is an enlarged partial perspective view of the algae outlet of the system of FIG. 1.

FIG. 7 shows a close up view of the outlet valve 131 used to harvest algae from photobioreactor system 5. To harvest the algae being cultivated, valve 131 may be opened to allow for the culture to drain from the photobioreactor system 5, such as through a hose. Typically, harvesting involves removing about one-third to about one-half of the culture in the system 5. Alternately, harvesting may be performed as a continuous or quasi-continuous process, such as by frequently extracting small quantities (such as on the order of a gallon or so), which has the advantage of keeping the algae density high. After exiting photobioreactor system 5, the algae can be removed from the media water through any number of ways known in the art. As discussed above, the media water may be recycled and used to refill the photobioreactor system 5.

As shown in FIGS. 8A-9B, another embodiment of the photobioreactor system 50 replaces the array of tubes and the rigid top manifold and rigid bottom manifold with a single-piece bag construction made from a thin, inexpensive film. Similar to the films used to create the tubes 12, the film used to construct the single-piece bag photobioreactor 50 typically exhibits a tensile strength sufficient to hold the liquid media under the system's 50 operating temperatures, some degree of UV radiation resistance, durability when being handled, visible light transparency; and stretching characteristics that prevent the formation of a tear-drop shape or the tubes 12 from pillowing-out when the tubes 12 are filled. In the single-piece bag photobioreactor 50, the film is typically selected to maintain the desired structural dimensions of the system 50 when filled. Suitable films that can be used include, but are not limited to, the previously described LDPE, ETFE, or PET films.

The single-piece bag photobioreactor system 50 comprises a plurality of vertical tubes 52 of the same general construction as the tubes 12 of the previous embodiment. While tubes 52 are all part of the single-piece or unitary bag photobioreactor 50, tubes 52 are typically separated from one another by plastic seals or welds 54 that form the vertical walls of tubes 52 and define open spaces 53. The single-piece bag photobioreactor 50 replaces the rigid manifolds of photobioreactor system 5 and incorporates a top manifold portion 56 and bottom manifold portion 58 into the single-bag construction, so that each of the top and bottom manifolds 56, 58 are defined by horizontal tubes 52 formed in the film. In producing the single-piece bag design for photobioreactor 50, the tops of tubes 52 are integral with and open to top manifold 56 and the bottom of tubes 52 are integral with, and open to, top manifold 56 to form fluid and gas pathways, so that fluid and gas can pass through each of the tubes 52 and into and out of respective top and bottom manifolds 56, 58.

While this embodiment has multiple tubes 52 separated by welds 54 and open spaces 53, it will be appreciated that various structures and methods of manufacturing the photobioreactor system 50 can be used. For example, photobioreactor system 50 can be constructed from a single sheet of plastic, where the sheet of plastic is folded in half and a set number of welds 54 and wishbone cuts 53 are made to define the tubes 52 and manifolds 56, 58. Alternatively, the sheet of film can be pressed into a mold to form the tubes 52 and manifolds 56, 58 or each of the components (e.g., the tubes 52 and manifolds 56, 58) can individually be blow molded or the like and then assembled together to form the photobioreactor system 50. No matter the method of construction used, the photobioreactor system 50 is also typically equipped with enough rigid ports to support at least one exhaust valve, gas inlet valve, water inlet valve, and water outlet valve. These valves are used in the same manner as discussed in association with photobioreactor system 5, so that the photobioreactor system 50 is a substantially closed, aseptic system, typically operated under positive pressure to prevent or minimize the introduction of contaminants in the system.

As discussed in association with tubes 12 for photobioreactor system 5, tubes 52 can be of any desired length that can be managed during the algae production process. While tubes 52 can be of any desired length, tubes 52 in this embodiment are typically about 10 feet long and typically range between about 5 to about 15 feet in length. Similarly, while tubes 52 may have diameters of any convenient size that can easily be managed during the algae production process, tubes 52 in this embodiment typically have diameters ranging from about 1 to about 2 inches. In addition, while the width of the single-piece bag photobioreactor system 50 can be any convenient width, it is typical that the width of the system 50 is between about 10 and about 100 feet.

Single-piece bag photobioreactor system 50 typically has a plastic margin that includes a plurality of vertical cutouts or slots. The plastic margin 60 is typically sufficient size and structural strength to support the weight of the entire photobioreactor system 50 when filled with fluid. The single-piece bag photobioreactor system 50 may be connected to the top rail 24 of a frame 21 by any number of mechanisms known in the art, including, but not limited to, threading wire riggings 14 through slots to hang the system 50 from top rail 24 or fixing a plurality of hooks on top rail 24 and threading the hooks through slots to hang the system 50 from the top rail 24.

Figure 8B:
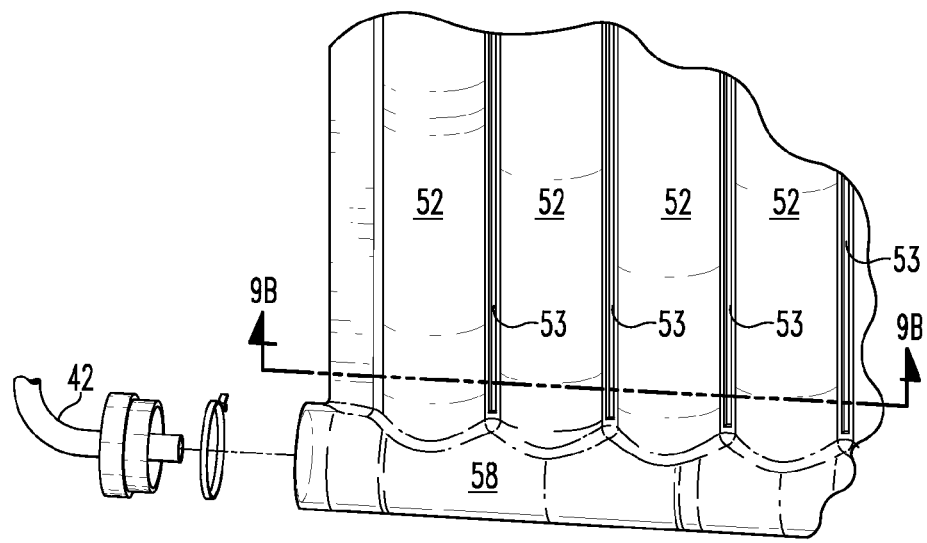
FIG. 8B is an enlarged partial view of FIG. 8A.
Figure 9B:
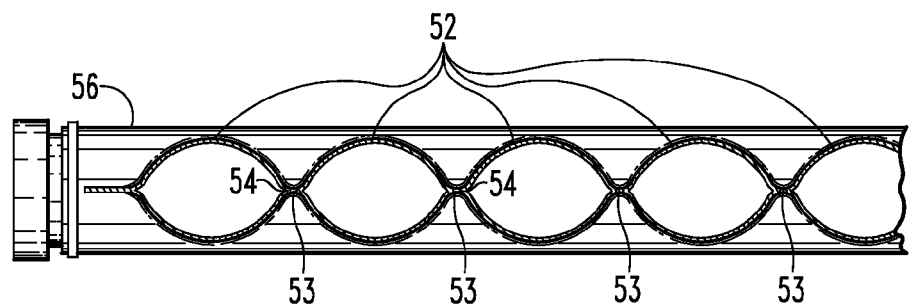
FIG. 9B is a sectional view of the photobioreactor system of FIG. 8B.
Figure 9A:
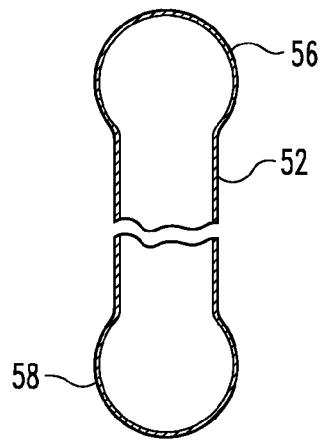
FIG. 9A is a sectional view of the photobioreactor system of FIG. 8A.
Figure 10:
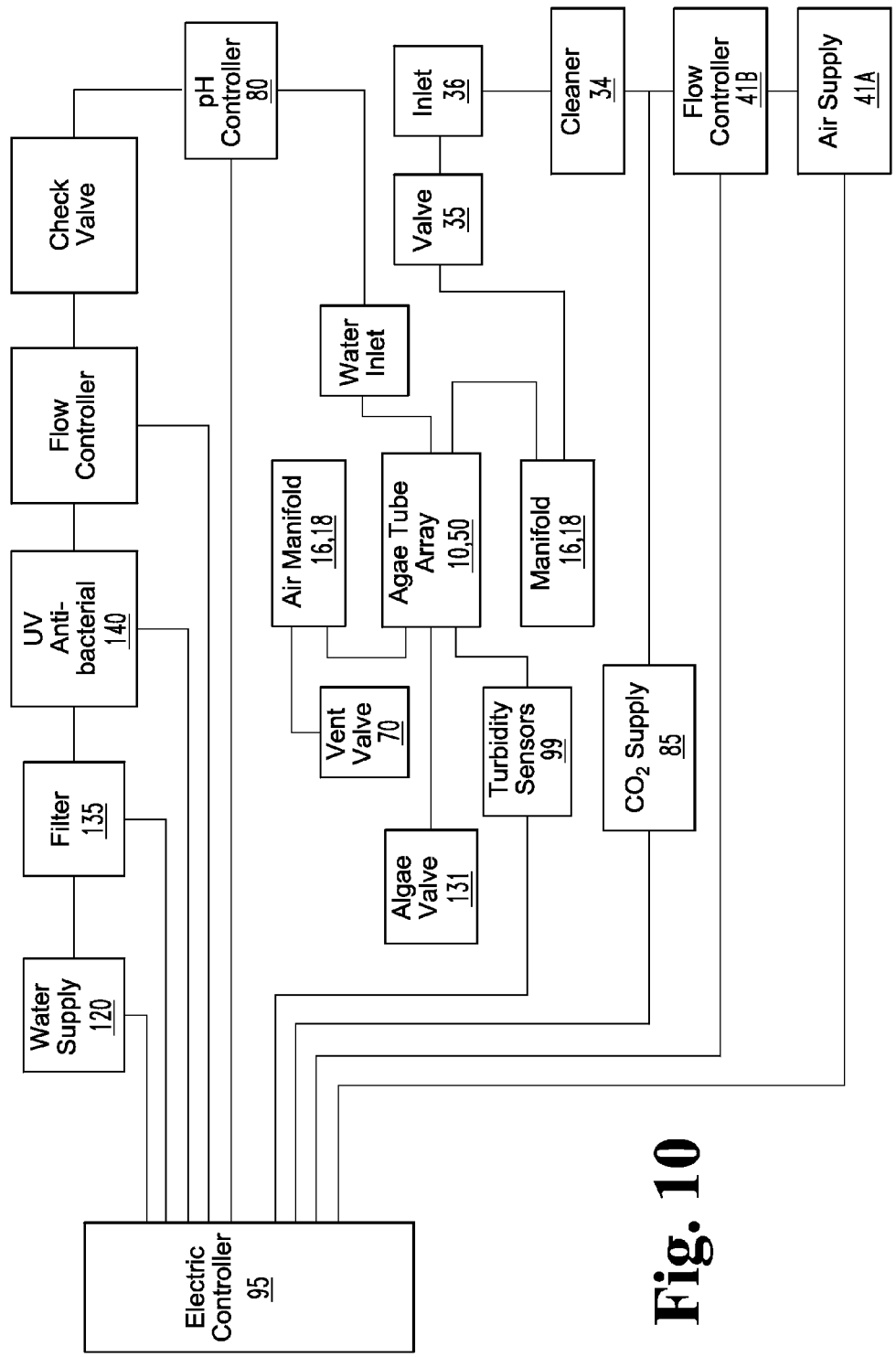
FIG. 10 is a schematic view of the embodiments of FIGS. 1 and 8A.

FIGS. 9A and 9B show cross-sectional views of the single-piece bag photobioreactor system 50 along sections A-A and B-B of FIGS. 8A and 8B, respectively. Section B-B provides a view of the bottom/lower manifold 58 and diagrams the flow of liquid and gas from the bottom manifold 58 through tubes 52. An aeration tube 42 is positioned within lower manifold 58. While the lower manifold 58 can have any size diameter, the lower manifold 58 of this embodiment has a diameter of about 3 to 4 inches. Aeration tube 42 allows for bubbles to form along the length of the tube 52. It is important that the aeration tube 42 is selected so that the bubbles provided to the culture in tubes 52 do not give rise to shear damage to the algae, and also provide enough surface area for effective gas exchange. For example, if the bubbles are too small (i.e., smaller than the cells of the algae culture) the bubbles will enter the culture at a high velocity and may cause shear damage to the algae. Further, if the bubbles are too large, there will not be enough surface area for effective gas exchange. It has been found that a paper diffuser, such as those made commercially available by AquaticEco Systems, can serve as an effective aeration tube 42 and be used to provide bubbles with the desired size.

The air bubbles from an air supply 41A leave the aeration tube 42, entering into the culture, and traveling up through tubes 52. Flow rate is typically determined by a flow controller 41B connected in line between the air supply and the air cleaner 34. As the bubbles leave the aeration tube 42 and travel through the tubes 52, the air urges the culture to stir and creates turbulence in the respective tubes 52. As a result, tubes 52 self-organize into a set of up-flows and down-flows with the mixing occurring between them in the top and bottom manifolds 56, 58. The constant mixing keeps nutrients evenly dispersed, keeps gas well dissolved, and keeps algae from precipitating or sticking to the surfaces of tubes 52 or the manifolds 56 and 58. Thus, unlike other prior art systems that use additional components, such as pumps, to mix the culture and create turbulence, photobioreactor system 50 does not require anything else than the pressurized air to be delivered through the aeration tube 42 to promote mixing of the culture and create turbulence.

The pressure of the air being provided only needs to exceed the pressure of tube 52 that is filled with culture (e.g., for a 10 feet tube—4 to 5 psi), plus the head resistance of the aeration tube 42, (e.g., for a paper diffuser about 0.5 psi) and the excess pressure for the inlet air valve (e.g., about 0.5 psi), and finally, any head loss in the air delivery tubing and filter used to deliver the air to the culture. Thus, air delivery systems that are able to deliver air in the range of at least about 6 psi to 8 psi would be sufficient for use in this embodiment. Such air delivery systems can include, but are not limited to, a roots blower system, an array of fan blowers, or an air compressor. The air delivery system can be connected to the lower manifold 58 by gas inlet tube 36 (See FIG. 6).

Air delivery systems typically deliver the gas at a constant air flow rate that will largely be dependent on the diameter of a tube 12, 52. For example, a one third reduction in tube diameter yields a one-half reduction in the air volume requirements. A single tube 12, 52 that has a diameter of 45 millimeters should have a flow rate of about 4 to 5 liters per hour. Accordingly, the air flow rate for the photobioreactor system 5, 50 can be calculated by multiplying the number of tubes 12, 52 that are part of the system 5, 50 by the requisite flow rate. If the system 5, 50 contains fifty tubes 12, 52, each with a diameter of 45 millimeters, the air flow rate of the system 5, 50 should be in the range of about 200 to 250 liters per hour. It will be appreciated that the desired air flow rate can be calculated in a similar manner for larger or smaller applications.

Photobioreactor system 5, 50 is typically equipped with a pH probe to monitor the pH levels of the culture. Evolved oxygen from photosynthesis under lighted conditions contributes to alkalinity of the culture. To maintain approximately neutral pH for promotion of algae growth, the excess evolved oxygen is typically substantially continuously removed. In addition, the pH can be controlled by introducing additional carbon dioxide from $CO_2$ source 85 to lower the pH. The pH probe is in electronic communication with a controller 80 that is operationally connected to at least one solenoid. The controller 80 and solenoid govern when additional carbon dioxide is added to the air being fed to the photobioreactor system 5, 50.

Flue gas from a carbon dioxide producer (e.g., a coal fired plant) could serve as the carbon dioxide source 85 and be fed at the desired pressures (i.e., 6 psi to 8 psi) to the photobioreactor system 50 through gas inlet tube 36 and aeration tube 42. Alternately, any convenient $CO_2$ source may be used to achieve a high $CO_2$ partial pressure gas mixture for bubbling through the bioreactor system 50. When using a flue gas stream, it would likely be necessary to strip some of the carbon dioxide from the stream and/or to provide a nitrogen stream for aeration of the culture. Alternately, the flue gas stream may be diluted with air or nitrogen. Due to the high concentrations of carbon dioxide in flue gas, too much carbon dioxide could be absorbed in the culture, which could lead to increased acidity. If left uncontrolled, the low pH could inhibit algae growth or even kill micro-algae. It will be appreciated by one of ordinary skill in the art that there are a number of ways that some of the carbon dioxide can be removed from the flue gas stream. For example, one way to usefully decrease the concentration of the carbon dioxide would be by running the flue gas through an aqueous ammonia solution before supplying it to the photobioreactor 5, 50.

In addition to adding carbon dioxide to the culture, aeration assists in the removal of the excess evolved oxygen produced from photosynthesis. Typically, the top/upper manifold 16, 56 is of sufficient size to not be completely filled with fluid when the photobioreactor system 5, 50 is in use. In this manner, an air space is generated in top manifold 56. While the top manifold 56 may have any convenient diameter size, the top manifold 56 used in this embodiment has a diameter typically ranging from about 4 to about 6 inches.

The air bubbles flow up from aeration tube 42, pass through the media in tubes 52, and then exit the media in the upper manifold 16, 56 into the airspace. As the air flows in this manner, carbon dioxide is introduced into the system 50 and absorbed by the algae during photosynthesis, and oxygen is generated and released to air space 40. One or more (typically one-way), exhaust check valves 70 are placed on the end of the upper manifold 16, 56 to allow the excess oxygen to escape the photobioreactor system 50 when the pressure exceeds 0.5 PSI. By venting the oxygen in this manner, the pH levels may be controlled and the growth of algae may be optimized.

While the forgoing discussion refers to the flow of fluid, algae and gas through the single-piece bag photobioreactor 50, it will be appreciated that photobioreactor system 5 allows for the flow of fluid, algae and gas in between its vertical tubes 12 and top and bottom manifolds 16 and 18 in the same manner that the fluid, algae and gas flow through photobioreactor system 50. It will also be appreciated that the bottom manifold 18 of photobioreactor system 5 also has an aeration tube 42 and the top manifold 16 also has an air space 40 as described above. In this manner, the culture is continuously mixed at the top and bottom manifolds 16, 18 and throughout the tubes 12. The substantially constant mixing keeps nutrients evenly dispersed, keeps gas well dissolved, and keeps algae from precipitating or sticking to the surfaces of tubes 12 or the manifolds 16, 18.

The maximum density obtainable in the algae culture in a photobioreactor system 5, 50 is generally related to the availability of light and nutrients and the micro-algae species under cultivation. Nutrients are taken up by organisms at varying rates. As known to those skilled in the art, nutrient starvation, high or low temperatures, and under or over-concentration of biomass left uncontrolled can inhibit the growth of or even kill micro-algae. To prevent under or over-concentration of biomass in the photobioreactor system 5, 50, the concentration of micro-algae may be measured such as by using turbidity. To reduce the concentration of biomass in the culture, a portion of the biomass is harvested and the culture is diluted with fresh media. The ideal dilution rates correspond to the cellular generation time or growth rates. Typically, harvest and dilution is carried out during the light period and is halted during the night when little additional biomass is being produced. Any means known in the art can be used to measure the turbidity of the culture. For example, turbidity sensors 99 can be added to the photobioreactor system 5, 50 to continually monitor the turbidity levels. Such sensors can be in electronic communication with a controller that controls one or more solenoids. The controller and solenoids can be used to govern the media inlet valves and harvesting outlet valves. When the turbidity reaches a predetermined set point, the controller and solenoid can be used to open the media inlet valve and harvesting outlet valve, so that fresh media can be added to the photobioreactor system 5, 50 and a portion of the culture can be harvested to dilute the culture to the desired turbidity.

In addition to controlling pH levels and the concentration of biomass, the temperature of the photobioreactor system 5, 50 needs to be maintained as well. The particular algae strain being cultivated will dictate the range of temperatures that will need to be optimally maintained for the culture. Any number of technologies can be used to make sure the culture is grown in the desired temperatures. For example, the heat of the surrounding environment can be controlled through any number of known methods or a heat exchanger can be positioned within the bottom manifold 18, 58 to allow for the culture to be heated or cooled.

To produce algae on a large scale, several photobioreactors 5, 50 can be set up on a farm to optimize the light available to algae and thereby maximize culture density. Algae grows best in low light levels, so it is preferred to configure the farm to position the photobioreactors 5, 50 in a pattern that will keep the light levels that will optimize the growth of the species of algae being grown. For example, if *Botryoccus brauni* (Bb) is the species of algae being cultivated, the photobioreactors can be positioned in a pattern that will keep the light levels down to $\frac{1}{10}^{th}$ or $\frac{1}{20}^{th}$ of full sunlight and/or to maintain the light intensities below 250 W/m$^2$ over significant proportions of the bioreactor surface. For this species, it is preferred that the photobioreactors 5, 50 are positioned to maintain light intensities in the range of 60 to 120 W/m$^2$.

At its maximum intensity on the ground, sunlight has a light intensity between about 1,000 W/m$^2$ to about 2,000 W/m$^2$. Thus, to reduce the maximum light intensity to about 100 W/m$^2$ requires an increase in surface area of about a factor of ten. Based on 1 inch diameter bioreactor tubes 12, 52, a square meter of vertically hanging array of tubes 12, 52 would hold approximately 12.7 liters of fluid. Thus, spreading the light through ten square meters would provide a specification of 127 liters of culture per square meter or 513,951 liters per acre. By using 10 foot high, 2 inch in diameter bioreactor tubes 12, 52, the photobioreactor systems 5, 50 can have an array 10, 50 of about fifty bioreactor tubes 12, 52 per square meter. Keeping in mind these specifications, the vertically hanging tubes 12, 52 can then be equally spaced horizontally over a distance of about thirty feet to achieve the desired light intensities. It will be appreciated by those of ordinary skill in the art that as the length of the tubes 12, 52 increase, the spacing between the tubes 12, 52 should also increase and likewise, as the length of the tubes 12, 52 is decreased, the spacing between the tubes 12, 52 should decrease to achieve the desired light intensities.

To assist in maintaining the desired light intensities, the horizontal X-axis of the photobioreactors 5, 50 should be oriented along the north-south direction, if sunlight is a contributing light source. This orientation helps keeps the light made available to the photobioreactor system 5, 50, indirect, diffuse, and evenly spread the over more of the photobioreactor 5, 50 area. Moreover, when using multiple photobioreactors 5, 50, the photobioreactors 5, 50 should be positioned relative to each other to assist in optimizing the light for each photobioreactor system 5, 50. For example, it is preferred that photobioreactor systems 5, 50 having 10 foot high, 2 inch in diameter bioreactor tubes 12, 52 be positioned in parallel rows (See FIG. 3A) with a distance of about two feet in between the rows. To further optimize the light, the surrounding structural members and the ground can be covered with reflective materials to prevent absorption of useful light by the structural members and the ground.

It will be appreciated that the photobioreactors 5, 50 described herein can be used to grow virtually any desired algae strains. Typically, the selected algae will be one that grows quickly and can provide a relatively high yield of oil. For example, *Botryoccus brauni* (Bb), *Botryoccus sudeticus* (Bs), *Scenedesmus dimorphus* (Sd), *Scenedesmus obliquus* (So), *Nannochloropsis occulata* (NanO) and *Neochloris oleoabundans* (No) are common strains of algae that have been identified as good sources of algae oil. Further, algae strains may be quickly and efficiently grown to yield other byproducts in addition to fuel oil, such as pharmaceuticals, food protein, and the like.

While the disclosed technology has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the claimed technology are desired to be protected.

We claim:

1. A bioreactor assembly for culture of photoautotrophic algae, comprising:
    a first substantially horizontal manifold;
    a second substantially horizontal manifold positioned below the first manifold;
    a collection of substantially parallel, substantially transparent tubes extending between the first manifold and the second manifold such that each tube is oriented substantially vertically and substantially perpendicular to the first manifold and substantially vertical and substantially perpendicular to the second manifold;
    an air supply operationally connected to the second manifold;
    a water purifier operationally connected to at least one manifold;

a water supply operationally connected to at least one water sterilizer;

a pH sensor positioned to measure a pH level in at least one of the tubes; and an electronic controller operationally connected to the pH sensor, the air supply, the water purifier, and the water supply;

wherein each tube is connected in fluidic communication with the first horizontal manifold;

wherein each tube is connected in fluidic communication with the second horizontal manifold; and wherein each transparent tube is composed of a polymer film chosen from a group consisting of low density polyethylene (LDPE), ethylene tetraflouride (ETFE), polyethylene teraphalate (PET), or combinations thereof.

2. The apparatus of claim 1 wherein the air supply includes a selectively actuatable $CO_2$ supply.

3. The apparatus of claim 1 wherein the collection, the first manifold, and the second manifold are all formed from a unitary plastic film.

4. The apparatus of claim 1 wherein the first manifold and the second manifold are substantially rigid and substantially cylindrical in shape, and wherein the tubes are formed from sheets of flexible polymers.

5. The apparatus of claim 1 wherein the water purifier is selected from the group consisting of: a water filter, a water sterilizer, and a combination thereof.

6. A bioreactor system for culture of photoautotrophic algae, comprising:

a plurality of elongated, substantially vertical, and substantially transparent tubes formed in a unitary piece of plastic film, wherein each elongated tube has an upper end and a lower end, wherein each tube is positioned adjacent and substantially parallel to another tube, and wherein boundaries of each tube are formed from a collection of welds made to the plastic film;

a first manifold formed in the plastic film, the first manifold being in fluid communication with the upper end of each tube to define a first plurality of pathways that allow for fluid and gas to flow in between each tube and the first manifold tube, wherein each tube is oriented substantially vertically and substantially perpendicular to the first manifold tube; and a second manifold formed in the plastic film, the second manifold being in fluid communication with the lower end of each tube to define a second plurality of pathways that allow for fluid and gas to flow in between each tube and the second manifold, wherein each tube is oriented substantially vertically and substantially perpendicular to the second manifold, and the first manifold and the second manifold are oriented substantially parallel to each other.

7. The bioreactor system of claim 6 wherein the first manifold has a water inlet connection formed therethrough.

8. The bioreactor system of claim 7, further comprising:
at least one air exhaust valve operationally connected to the first manifold.

9. The bioreactor system of claim 6, further comprising:
an air circulation system operationally connected to the second manifold; and
a water circulation system operationally connected to the first manifold.

10. The bioreactor system of claim 9 wherein the air circulation system further comprises a $CO_2$ supply.

11. The bioreactor system of claim 10, further comprising an electronic controller operationally connected to the air circulation system and to the water circulation system; and wherein the tubes and the first manifold and the second manifold are substantially filled with water; and wherein the electronic controller functions to regulate water pH.

12. The bioreactor system of claim 6 wherein the first manifold, the second manifold, and each transparent tube are composed of a polymer film chosen from a group consisting of low density polyethylene (LDPE), ethylene tetraflouride (ETFE), polyethylene teraphalate (PET), or combinations thereof.

* * * * *